US011850218B2

(12) United States Patent
Weiss

(10) Patent No.: US 11,850,218 B2
(45) Date of Patent: *Dec. 26, 2023

(54) NUTRACEUTICAL COMPOSITIONS AND METHODS FOR DIETARY ALLEVIATION OF POLYCYSTIC OVARY SYNDROME

(71) Applicant: Provation Life LLC, Beit Shemesh (IL)

(72) Inventor: Herman Weiss, Beit Shemesh (IL)

(73) Assignee: Provation Life LLC, Beit Shemesh (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/121,679

(22) Filed: Mar. 15, 2023

(65) Prior Publication Data

US 2023/0372266 A1 Nov. 23, 2023

Related U.S. Application Data

(60) Provisional application No. 63/342,957, filed on May 17, 2022.

(51) Int. Cl.
| | |
|---|---|
| *A61K 31/12* | (2006.01) |
| *A23L 33/14* | (2016.01) |
| *A23L 33/105* | (2016.01) |
| *A23L 33/16* | (2016.01) |
| *A61K 36/54* | (2006.01) |
| *A61K 45/06* | (2006.01) |
| *A61P 15/08* | (2006.01) |
| *A61K 31/4745* | (2006.01) |
| *A61K 33/24* | (2019.01) |
| *A61K 31/047* | (2006.01) |
| *A23L 33/00* | (2016.01) |
| *A23L 33/125* | (2016.01) |
| *A61K 31/366* | (2006.01) |

(52) U.S. Cl.
CPC ............ *A61K 31/12* (2013.01); *A23L 33/105* (2016.08); *A23L 33/125* (2016.08); *A23L 33/14* (2016.08); *A23L 33/16* (2016.08); *A23L 33/40* (2016.08); *A61K 31/047* (2013.01); *A61K 31/366* (2013.01); *A61K 31/4745* (2013.01); *A61K 33/24* (2013.01); *A61K 36/54* (2013.01); *A61K 45/06* (2013.01); *A61P 15/08* (2018.01)

(58) Field of Classification Search
None
See application file for complete search history.

(56) References Cited

U.S. PATENT DOCUMENTS

2005/0147620 A1* 7/2005 Bozicevic ............ A61K 31/455
514/592
2015/0297536 A1* 10/2015 Deshpande ............ A61P 43/00
514/679

2017/0035728 A1* 2/2017 Bagchi ................. A61K 31/385
2021/0100866 A1 4/2021 Crane
2022/0047665 A1 2/2022 Gubler et al.

FOREIGN PATENT DOCUMENTS

| FR | 3125409 A1 * | 1/2023 |
| WO | WO2014/135956 | 9/2014 |
| WO | WO2014135956 | 9/2014 |

OTHER PUBLICATIONS

Klimek et al. Safety and Efficacy of Red Yeast Rice (*Monascus purpureus*) as an Alternative Therapy for Hyperlipidemia 2009.*
Diebacinn Cholesterol Jun. 24, 2017.*
Leo et al. "A combined Treatment with Myo-Inositol and Monacolin K Improve the Androgen and Lipid profiles of Insulin-Resistant PCOS Patients" 2013.*
Red yeast rice. Wayback machine date Feb. 2, 2018.*
Pasquali et al., "Secondary Polycystic Ovary Syndrome: Theoretical and Practical Aspects," European Journal of Endocrinology, Nov. 27, 2021.
Leo et al., "A Combined Treatment with Myo-Inositol and Monacolin K Improve the Androgen and Lipid Profiles of Insulin-Resistant PCOS Patients," Journal of Metabolic Syndrome, 2013.
Chien et al., "Effects of Curcumin on Glycemic Control and Lipid Profile in Polycystic Ovary Syndrome: Systematic Review with Meta-Analysis and Trial Sequential Analysis," https://doi.org/10.3390/nu13020684. Feb. 21, 2021.
Giampaolino et al., "Microbiome and PCOS: State-of-Art and Future Aspects," https://www.mdpi.com/journal/ijms, Feb. 19, 2021.
Unfer et al., "Effects of Inositol(s) in Women with PCOS: A Systematic Review of Randomized Controlled Trials," International Journal of Endocrinology, Sep. 22, 2016.
Merviel et al., "Impact of myo-inositol treatment in women with polycystic ovary syndrome in assisted reproductive technologies," https://reproductive-health-journal.biomedcentral.com/articles/10.1186/s12978-021-01073-3, Jan. 19, 2021.

(Continued)

*Primary Examiner* — Danah Al-Awadi
(74) *Attorney, Agent, or Firm* — Weiss & Arons LLP

(57) ABSTRACT

Compositions and methods for nutraceutical compositions and methods for dietary alleviation of polycystic ovary syndrome (PCOS). Compositions may include at least one anti-hyperandrogenism ingredient. Compositions may include at least one insulin-sensitivity modulating ingredient. The anti-hyperandrogenism ingredient may include inositol. The anti-hyperandrogenism ingredient may include monacolin K (red yeast). The insulin-sensitivity modulating ingredient may include inositol. The insulin-sensitivity modulating ingredient may include curcumin. The methods may include oral administration of the compositions. The methods may include physician monitoring of symptoms during use of the compositions. Case studies demonstrate positive benefits of application of the compositions and methods in alleviation of PCOS. Demonstrated benefits include conception after lengthy infertility prior to application of the compositions and methods. The methods may include formulation into a single over-the-counter composition for use in a supplement that a patient may self-administer in the treatment of PCOS, improvement of menstrual cyclicity and reversal of infertility.

1 Claim, No Drawings

(56) References Cited

OTHER PUBLICATIONS

Fontana et al., "The Deep Correlation between Energy Metabolism and Reproduction: A View on the Effects of Nutrition for Women Fertility," www.mdpi.com/journal/nutrients, Feb. 11, 2016.
Baldassarre et al., "Dysbiosis and Prematurity: Is There a Role for Probiotics?" www.mdpi.com/journal/nutrients, Jun. 5, 2019.
Lopez-Moreno et al., "Probiotics Dietary Supplementation for Modulating Endocrine and Fertility Microbiota Dysbiosis," www.mdpi.com/journal/nutrients, Mar. 13, 2020.
Calcaterra et al., "Polycystic Ovary Syndrome in Insulin-Resistant Adolescents with Obesity: The Role of Nutrition Therapy and Food Supplements as a Strategy to Protect Fertility," https://doi.org/10.3390/nu13061848, May 28, 2021.
Gunalan et al., "The effect of nutrient supplementation in the management of polycystic ovary syndrome-associated metabolic dysfunctions: A critical review," Journal of the Turkish-German Gynecological Association published by Galenos Publishing House, Oct. 8, 2018.
Arentz et al., "Nutritional supplements and herbal medicines for women with polycystic ovary syndrome; a systematic review and meta-analysis," BioMed Central, 2017.
Barthelmess et al., "Polycystic ovary syndrome: Current status and future perspective," National Institute of Health, Feb. 26, 2015.
Menon et al., "Antioxidant and anti-inflammatory properties of curcumin," https://link.springer.com/chapter/10.1007/978-0-387-46401-5_3, PubMed, 2007.
Wang et al., "Current Concepts About Chromium Supplementation in Type 2 Diabetes and Insulin Resistance," Springer Science+Business Media, LLC, Mar. 2, 2010.
Nasiadek et al., "The Role of Zinc in Selected Female Reproductive System Disorders," https://www.mdpi.com/2072-6643/12/8/2464, Aug. 16, 2020.
Hamilton et al., "Insulin Resistance and Serum Magnesium Concentrations among Women with Polycystic Ovary Syndrome," https://www.ncbi.nlm.nih.gov/pmc/articles/PMC6822014/pdf/nzz108.pdf, Oct. 3, 2019.
Yang et al., "Berberine improves insulin sensitivity by inhibiting fat store and adjusting adipokines profile in human preadipocytes and metabolic syndrome patients," https://www.ncbi.nlm.nih.gov/pmc/articles/PMC3310165/pdf/ECAM2012-363845.pdf, 2012.
Doggrell, "Berberine-a novel approach to cholesterol lowering," Expert Opinion on Investigational Drugs, May 31, 2005.
Papaleo et al., "Myo-inositol in patients with polycystic ovary syndrome: a novel method for ovulation induction," https://pubmed.ncbi.nlm.nih.gov/17952759/, Dec. 2007.
Dou et al., "The effect of cinnamon on polycystic ovary syndrome in a mouse model," Reproductive Biology and Endocrinology, file:///C:/Users/MiriRosengarten/Downloads/The_effect_of_cinnamon_on_polycystic_ovary_syndrom.pdf, 2018.
"Balance PCOS Multivitamin Formula", Retrieved on or before Feb. 14, 2022.
G. Morgante et al., "Polycystic Ovary Syndrome (PCOS) and Hyperandrogenism: The Role of a New Natural Association," Minerva Ginecologica, https://pubmed.ncbi.nlm.nih.gov/264918241, Oct. 2015.
MC Musacchio et al., "Evaluation of the myoinositol-monacholin K association on hyperandrogenism and lipid metabolism parameters in women," Minerva Medica Editions, Feb. 2013. English (google translate) and Italian versions attached herewith.).
Richard SL. 8th. Philadelphia: Lippincott Williams & Wilkins; 2003. Androgen excess disorders. Danforth's Obstetrics and Gynecology; https://doctorlib.info/gynecology/obstetrics/37.html, pp. 663-672. Chapter 37. RA.
Johansson J, Stener-Victorin E. Polycystic ovary syndrome: effect and mechanisms of acupuncture for ovulation induction. *Evid Based Complement Alternat Med*. 2013;2013:762615.
"Everything You Need to Know About Berberine," https://www.medicalnewstoday.com/articles/325798#benefits, Jun. 12, 2023.
Morshed et al., "Luteinizing Hormone to Follicle-Stimulating Hormone Ratio Significantly Correlates with Androgen Level and Manifestations are more Frequent with Hyperandrogenemia in Women With Polycystic Ovary Syndrome," https://www.jofem.org/index.php/jofem/article/view/716/284284502, Journal of Endocrinology and Metabolism, Feb. 2021.
International Search Report and Written Opinion for International Application No. PCT/US2023/022230, dated Oct. 19, 2023.
Derosa et al., "An Evaluation of a Nutraceutical with Berberine Curcumin, Inositol, Banaba and Chromium Picolinate in Patients with Fasting Dysglycemia," vol. 13, pp. 653-661 https://www.ncbi.nlm.nih.gov/pmc/articles/PMC7060772/, Published online Mar. 3, 2020.
Karandish et al., The Effect of Curcumin and Zinc Co-supplementation on Glycemic Parameters in Overweight or Obese Prediabetic Subjects: A Phase 2 Randomized, Placebo—controlled Trial with a Multi-arm, Parallel-Group Design, https://www.researchgate.net/publication/351092023_The_effect_of_curc_umin_and_zinc_co_supplementation_on_glycemic_parameters_in_overweight_or_obese_prediabetic_subjects_A_phase_2_randomized_placebo-controlled_trial_with_a_multi-arm_parallel-group_desi, Phytotherapy Research, Apr. 2021.

\* cited by examiner

NUTRACEUTICAL COMPOSITIONS AND METHODS FOR DIETARY ALLEVIATION OF POLYCYSTIC OVARY SYNDROME

CROSS-REFERENCE TO RELATED APPLICATION

This application is a non-provisional of U.S. Provisional Patent No. 63/342,957, filed on May 17, 2022, entitled, "NUTRACEUTICAL COMPOSITIONS AND METHODS FOR DIETARY ALLEVIATION OF POLYCYSTIC OVARY SYNDROME," which is hereby incorporated by reference herein in its entirety.

FIELD OF TECHNOLOGY

Aspects of the disclosure relate to treatment of Polycystic Ovary Syndrome (PCOS). In particular, the disclosure provides compositions of and methods for dietary supplementation directed to alleviation of symptoms of PCOS. A focus of the disclosure is reversal through such dietary supplementation of PCOS-related infertility.

BACKGROUND OF THE INVENTION

Polycystic Ovary Syndrome (PCOS) affects many tens of millions of women worldwide. PCOS features disruption of normal female endocrine regulation of menstruation and ovulation cycles, resulting in irregular and difficult menses and/or in monthly production of multiple immature proto-ova within follicular cysts but usually no viable ovum. PCOS accounts for approximately 25% of the diagnoses of couples seeking treatment for infertility. Additionally, PCOS carries a significantly higher than usual risk of early termination of pregnancy and of other gestational complications such as dangerously elevated blood pressure. Left untreated, PCOS may lead to type 2 diabetes mellitus, coronary artery disease and/or endometrial hyperplasia, which latter carries a just sub-10% risk of cancer.

Well over half of PCOS patients present metabolic disorders related to insulin resistance, in which cells do not utilize insulin effectively to handle blood glucose levels, often manifesting as hyperinsulinemia and eventuating diabetes mellitus. PCOS is associated in over half of cases (overlapping but non-conterminous with the insulin-resistant patients) with hyperandrogenism, marked by heightened androgen (male sex hormone) levels in the female circulation. While underlying causes of PCOS are not clear, progress has been made in overcoming the syndrome's symptomatic menstrual, ovulatory and gestational complications through therapies that reduce insulin resistance. Similarly, such progress has been made through therapies that reduce hyperandrogenism.

Several drugs are in use for PCOS. Worldwide, these include acetates of chlormadinone, medroxyprogesterone and (except for the United Sates) cyproterone, all synthetic steroidal progestin agents utilized for their anti-androgenic effects. None has a noticeable effect on insulin resistance. They have demonstrated usefulness in regulating menstrual symptoms of PCOS, but some may lessen the likelihood of pregnancy. Cyproterone has been implicated in increased risk of intracranial meningioma, with a late-presenting possible outcome of increasing compression by the slowly growing meningeal tumors upon adjacent blood vessels, nerves and brain tissue.

Other drugs in use for PCOS include thiazolidinediones (glitazones) that target insulin resistance but not hyperandrogenism, but often produce side-effects of weight gain and fluid retention, with its possible consequences for cardiopulmonary congestion. Another adverse side-effect of thiazolidinediones, studied as of now only in elderly patients, is reduction in bone mineral density.

A drug in wide use for PCOS is metformin, a biguanide, which apparently targets both insulin resistance and hyperandrogenism. The majority of its current (early 2020's) worldwide 100+ million prescriptions is directed to treatment of diabetes, by a dual mechanism of lowering glucose release from the liver and of increasing cellular sensitivity to insulin. Use of metformin is associated with alleviation of PCOS's menstrual, ovulatory and gestational complications. However, use of metformin often produces adverse gastrointestinal side-effects, some quite severe, and, more rarely, potentially lethal lactic acidosis.

Accordingly, it would be desirable for alleviation of PCOS symptoms to provide compositions and methods that target insulin resistance, but without the adverse side-effects of metformin and other insulin-resistance modulating drugs. Likewise, it would be desirable for alleviation of PCOS symptoms to provide compositions and methods that target hyperandrogenism, but without the adverse side-effects of metformin and other anti-androgenic drugs.

With natural products having centuries-long track records of experience-based safe use and dosing levels, in contrast with modern pharmaceutical drugs' usage and safety/efficacy-testing records of decades, it would also be desirable for alleviation of PCOS symptoms to provide nutraceutical compositions and methods utilizing natural products.

Several natural products have been shown to produce beneficial effects countering insulin-resistance and/or hyperandrogenism, and without adverse side-effects. Thus, it would be desirable for alleviation of PCOS symptoms to provide nutraceutical compositions and methods that utilize a plurality of such natural products to achieve additive and possible synergistically positive effects. For enhanced compliance and consistency of dosing, it would further be desirable to have such plurality of natural products combined in a single composition directly ready, or easily readied, for oral consumption.

BRIEF DESCRIPTION OF THE DISCLOSURE

Compositions and methods for alleviation of PCOS symptoms are provided that combine several safe natural products, each with demonstrated beneficial effects countering insulin-resistance and/or hyperandrogenism.

The compositions may be used to perform steps of the methods. The methods may include oral self-administration of the compositions. The methods may include recurrent oral self-administration of the compositions. The methods may include pre-administration physician diagnosis of PCOS. The methods may include patient monitoring of symptoms before and during use of the compositions. The methods may include physician monitoring of symptoms during use of the compositions.

The methods may include formulation of the compositions into a single composition directly ready, or easily readied, for oral consumption. The single composition, comprising natural products with well-established safety profiles, may be available over-the-counter (hereinafter, "OTC"). Use of the single composition may allow for enhanced compliance and consistency of dosing in the treatment of PCOS, improvement of menstrual cyclicity and reversal of infertility.

The compositions and methods disclosed herein have been utilized in several case studies of PCOS patients with symptoms ranging from years of irregular menses to years of infertility. Use of the compositions and methods, with no exogenous hormonal treatment, yielded normal cyclicity of menses and, in the infertility cases, conception. Use of the compositions and methods has been continued after the positive results.

Technical effects of the compositions and methods, as confirmed in the case studies, include alleviation of clinical PCOS symptoms and reversal of anovulatory symptomology. Other aspects and advantages of the compositions and methods—including component amounts, compliance scheduling, and ease of administration; as well as significant positive psychological benefits accruing to patients—will be further appreciated from the following detailed description.

DETAILED DESCRIPTION OF THE DISCLOSURE

The compositions may be formulated to include readily bio-available forms of a plurality of natural products, each demonstrated to produce positive effects on either or both insulin-resistance and hyperandrogenism. Some of the natural products of the compositions have also been demonstrated to aid in reduction of body weight and, consequently, of Body Mass Index (BMI), where high BMI is a frequently encountered collateral symptom in a PCOS diagnosis. The methods may include recommended dosage amounts and scheduling of administration of the compositions, as well as use of probiotic, prebiotic and essentially fatty acid formulations, as well as of folate, each considered to positively contribute to good menstrual, ovulatory and/or gestational health.

The compositions may take the form of dietary supplement pills (tablets, capsules and/or caplets). The compositions may take the form of dietary supplement powders to be added to water or other potable fluids. The added powder may be mixed into the fluid. The resulting mixture may be further processed to prepare shakes or smoothies. The powders may be flavored. The compositions may take any other suitable form of dietary supplement. Other suitable forms of dietary supplement may include dietary supplement chews. The chews may be flavored. The chews may be formulated to be swallowed. The chews may be formulated as chewing gum with a gum base not intended to be swallowed.

The compositions may include inositol. The compositions may include cinnamon. The compositions may include curcumin. The compositions may include monacolin K (red yeast). The compositions may include chromium. The compositions may include zinc. The compositions may include magnesium. The compositions may include berberine. The compositions may include combinations of two or more of the above.

Inositols are sugar polyalcohols with several isomers, naturally occurring in fruit, nuts, corn and beans. One of those isomers, myo-inositol, is readily absorbed at the intestinal and cellular levels, and has been shown to produce a significant anti-androgenic effect, allowing rebalance of female sex hormones. Myo-inositol has also been shown to increase cellular sensitivity to insulin. Research has demonstrated myo-inositol's benefits in PCOS cases for restoration of normal menstruation, and for normal development of ovum and embryo. (Papaleo E, Unfer V, Baillargeon JP, De Santis L, Fusi F, Brigante C. Myo-inositol in patients with polycystic ovary syndrome: a novel method for ovulation induction. *Gynecol Endocrinol.* 2007;23:700-3)

Another naturally occurring isomer is D-chiro-inositol. The body may synthesize (epimerize) D-chiro-inositol from myo-inositol.

Cinnamon, used worldwide in cuisines, increases cellular sensitivity to insulin and is, therefore, widely used in controlling blood glucose levels. Cinnamon has been shown to improve menstrual cyclicity in PCOS cases. (Dou L, Zheng Y, Li L, et al. The effect of cinnamon on polycystic ovary syndrome in a mouse model. *Reprod Biol Endocrinol.* 2018;16(1):99. Published 2018 Oct 19. doi:10.1186/s12958-018-0418-y)

Curcumin, naturally occurring in the root-stalk of the turmeric plant, increases cellular sensitivity to insulin, apparently through lowering of blood lipid levels. (Chien, Y.-J.; Chang, C.-Y.; Wu, M.-Y.; Chen, C.-H.; Horng, Y.-S.; Wu, H.-C. Effects of Curcumin on Glycemic Control and Lipid Profile in Polycystic Ovary Syndrome: Systematic Review with Meta-Analysis and Trial Sequential Analysis. *Nutrients* 2021, 13, 684. https://doi.org/10.3390/nu13020684)

Curcumin's anti-oxidant/anti-inflammatory properties may be directly useful in ameliorating painful PCOS symptoms. (Menon VP, Sudheer AR. Antioxidant and anti-inflammatory properties of curcumin. *Adv Exp Med Biol.* 2007; 595:105-25. doi: 10.1007/978-0-387-46401-5_3. PMID: 17569207.)

Monacolin K, naturally occurring in red yeast and produced as a powder from white rice grown with red yeast, has been shown to inhibit steroid hormone production and provides an anti-androgenic effect. (Leo, Vincenzo. (2013). A Combined Treatment with Myo-Inositol and Monacolin K Improve the Androgen and Lipid Profiles of Insulin-Resistant PCOS Patients. *Journal of Metabolic Syndrome.* 02. 10.4172/2167-0943.1000127.)

With its statin anti-cholesterol mechanism of action, use of monacolin K may call for supplementation with coenzyme Q10 (CoQ10; ubiquinone), which may be included in the compositions. Use of monacolin K may also call for possible avoidance of concurrent use of high niacin doses or of prescription statins. Another statin-related consideration is that consumption of grapefruit may interfere with the effectiveness of the monacolin K.

Chromium, naturally occurring in numerous food types from broccoli to beef, is widely used in supplements as a blood glucose modulator, particularly in the form of chromium (III) picolinate, for its positive effect upon cellular sensitivity to insulin. Chromium picolinate also produces an anti-androgenic effect, lowering free testosterone levels in PCOS cases. (Wang ZQ, Cefalu WT. Current concepts about chromium supplementation in type 2 diabetes and insulin resistance. *Curr Diab Rep.* 2010; 10:145-51. [PubMed: 20425574])

Zinc and magnesium, naturally occurring in many foods and widely used as supplements with long-standing safety records, both show anti-androgenic effects.

Zinc supplementation has been shown to increase production of the female sex hormone progesterone, which is a natural androgen blocker. (Nasiadek M, Stragierowicz J, Klimczak M, Kilanowicz A. The Role of Zinc in Selected Female Reproductive System Disorders. *Nutrients.* 2020,12 (8):2464. Published 2020 Aug 16. doi:10.3390/nu12082464)

Magnesium supplementation seems to have a positive effect on production of lutenizing hormone, which plays significant roles in the menstrual cycle in general and ovulation in particular. (Hamilton KP, Zelig R, Parker AR, Haggag A. Insulin Resistance and Serum Magnesium Concentrations among Women with Polycystic Ovary Syndrome. *Curr Dev Nutr.* 2019;3(11):nzz108. Published 2019 Oct 3. doi:10.1093/cdn/nzz108)

Berberine, a widely used alkaloid extractable from many plants, often from Asiatic barberry bark, has been demonstrated to decrease insulin resistance as well as cholesterol levels, the latter through non-statin-like mechanisms. (Yang J, Yin J, Gao H. et al. Berberine improves insulin sensitivity by inhibiting fat store and adjusting adipokines profile in human preadipocytes and metabolic syndrome patients. *Evid Based Complement Alternat Med.* 2012;2012:363845. doi: 10.1155/2012/363845; Doggrell SA. Berberine—a novel approach to cholesterol lowering. Expert Opin *Investig Drugs*. 2005 May; 14(5):683-5. doi: 10.1517/13543784.14.5.683. PMID: 15926873.)

The bitterness of the berberine alkaloid may call for its formulation in powders or uncoated caplets/tablets to include sweeteners, such as stevia, and/or an intense masking flavor, such as chocolate.

Thus, each of the composition ingredients with demonstrated effectiveness in alleviating symptoms of PCOS targets either insulin resistance or hyperandrogenism, or targets both insulin resistance and hyperandrogenism. TABLE 1 accordingly lists each of those ingredients under one or both table categories of "insulin-sensitivity modulating" and "anti-hyperandrogenism," where an insulin-sensitivity modulating ingredient has been shown to produce a therapeutic effect of reducing insulin resistance and an anti-hyperandrogenism ingredient has been shown to produce a therapeutic effect of reducing male hormone levels.

TABLE 1

ACTIVITY CATEGORIES OF COMPOSITION INGREDIENTS

| INSULIN-SENSITIVITY MODULATING | ANTI-HYPERANDROGENISM |
|---|---|
| Inositol | Inositol |
| Chromium | Chromium |
| Curcumin | Monacolin K |
| Cinnamon | Zinc |
| Berberine | Magnesium |

Additional ingredients may include CoQ10. Additional ingredients may include potassium. Additional ingredients may include iron. Additional ingredients may include calcium. Additional ingredients may include any suitable component of supplementation recommended for optimizing menstrual, ovulatory or gestational health. Any such suitable component may include folate.

Additional ingredients may include probiotics. The probiotics may include *Bifidobacterium lactis*. The probiotics may include *B. lactis*. The probiotics may include lactic acid bacteria. The lactic acid bacteria may include *Lactobacilli*. The *Lactobacilli* may include *L. acidophilus*. The *Lactobacilli* may include *L. gasseri*. The probiotics may include any suitable species. Any suitable species may include *Lactobacillus johnsonii*. Any suitable species may include *Bacillus coagulans*.

Additional ingredients may include prebiotics. The prebiotics may include resistant dextrin. The prebiotics may include fiber. The fiber may include inulin.

Composition Combinations

Composition combinations include any combination of two or more of inositol, cinnamon, curcumin, berberine, monacolin K, chromium, zinc and magnesium, in any therapeutically effective mass range for each those ingredients.

The inositol may include a mixture of myo-inositol and D-chiro-inositol. The mixture of myo-inositol and D-chiro-inositol may feature myo-inositol to D-chiro-inositol in a mass ratio of about 80 to 1. The mixture may feature myo-inositol to D-chiro-inositol in a mass ratio of about 40 to 1. The mixture may feature myo-inositol to D-chiro-inositol in a mass ratio of about 20 to 1. The mixture may feature myo-inositol to D-chiro-inositol in any suitable mass ratio. Any suitable mass ratio of myo-inositol to D-chiro-inositol may include about 100 to 1.

Several of the composition combinations and mass ranges are now presented.

The composition combinations and mass ranges may constitute a dietary supplement for alleviation of symptoms of PCOS, with the supplement including a therapeutically effective amount of a combination of monacolin K (red yeast) and at least one other anti-hyperandrogenism ingredient. The amount may include a daily dosage amount.

The amount may include the monacolin K in a mass range from about 0.5 gram to about 4 grams. The mass range of monacolin K may be from about 1 gram to 3 about grams. The supplement may include CoQ10. The CoQ10 may be included at a mass range from about 0.5 milligram to about 4 milligrams.

The at least one other anti-hyperandrogenism ingredient may include a bio-assimilable form of zinc ($Zn^{2+}$). The amount may include the zinc ($Zn^{2+}$) in a mass range from about 10 milligrams to about 50 milligrams. The mass range of the zinc ($Zn^{2+}$) may be from about 20 milligrams to about 30 milligrams. The zinc ($Zn^{2+}$) may be included in the form of zinc citrate.

The at least one other anti-hyperandrogenism ingredient may include a bio-assimilable form of magnesium ($Mg^{2+}$). The amount may include the magnesium ($Mg^{2+}$) in a mass range from about 100 milligrams to about 500 milligrams. The mass range of the ($Mg^{2+}$) may be from about 200 milligrams to about 300 milligrams. The magnesium ($Mg^{2+}$) may be included in the form of magnesium citrate.

The at least one other anti-hyperandrogenism ingredient may include a bio-assimilable form of chromium ($Cr^{3+}$). The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The at least one other anti-hyperandrogenism ingredient may include inositol. The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The supplement may also include at least one insulin-sensitivity modulating ingredient.

The composition combinations and mass ranges may constitute a dietary supplement for alleviation of symptoms of PCOS, with the supplement including a therapeutically effective amount of a combination of curcumin and at least one other insulin-sensitivity modulating ingredient. The amount may include a daily dosage amount.

The curcumin may include curcuminoids in turmeric root extract. The amount may include the curcumin in a mass range from about 5 milligrams to about 2 grams. The mass range of the curcumin may be from about 10 milligrams to about 1500 milligrams.

The at least one other insulin-sensitivity modulating ingredient may include cinnamon. The cinnamon may include Ceylon cinnamon powder. The amount may include the cinnamon in a mass range from about 250 milligrams to about 1000 milligrams. The mass range of the cinnamon may be from about 400 milligrams to about 600 milligrams.

The at least one other insulin-sensitivity modulating ingredient may include berberine. The berberine may include extract of *Berberis aristata* bark. The amount may include the berberine in a mass range from about 5 milligrams to about 2000 milligrams. The mass range of the berberine may be from about 7.5 milligrams to about 1500 milligrams.

The at least one other insulin-sensitivity modulating ingredient may include a bio-assimilable form of chromium ($Cr^{3+}$). of chromium ($Cr^{3+}$). The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The at least one other insulin-sensitivity modulating ingredient may include inositol. The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The supplement may also include at least one anti-hyperandrogenism ingredient.

The composition combinations and mass ranges may constitute a dietary supplement for alleviation of symptoms of PCOS, with the supplement including a therapeutically effective amount of a combination of monacolin K (red yeast) and at least one insulin-sensitivity modulating ingredient. The amount may include a daily dosage amount.

The amount may include the monacolin K in a mass range from about 0.5 gram to about 4 grams. The mass range of monacolin K may be from about 1 gram to 3 about grams. The supplement may include CoQ10. The CoQ10 may be included at a mass range from about 0.5 milligram to about 4 milligrams.

The at least one insulin-sensitivity modulating ingredient may include curcumin. The curcumin may include curcuminoids in turmeric root extract. The amount may include the curcumin in a mass range from about 5 milligrams to about 2 grams. The mass range of the curcumin may be from about 10 milligrams to about 1500 milligrams.

The at least one insulin-sensitivity modulating ingredient may include cinnamon. The cinnamon may include Ceylon cinnamon powder. The amount may include the cinnamon in a mass range from about 250 milligrams to about 1000 milligrams. The mass range of the cinnamon may be from about 400 milligrams to about 600 milligrams.

The at least one insulin-sensitivity modulating ingredient may include berberine. The berberine may include extract of *Berberis aristata* bark. The amount may include the berberine in a mass range from about 5 milligrams to about 2000 milligrams. The mass range of the berberine may be from about 7.5 milligrams to about 1500 milligrams.

The at least one insulin-sensitivity modulating ingredient may include a bio-assimilable form of chromium ($Cr^{3+}$). of chromium ($Cr^{3+}$). The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The at least one insulin-sensitivity modulating ingredient may include inositol. The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The supplement may also include at least one other anti-hyperandrogenism ingredient.

The composition combinations and mass ranges may constitute a dietary supplement for alleviation of symptoms of PCOS, with the supplement including a therapeutically effective amount of a combination of curcumin and at least one anti-hyperandrogenism ingredient. The amount may include a daily dosage amount.

The curcumin may include curcuminoids in turmeric root extract. The amount may include the curcumin in a mass range from about 5 milligrams to about 2 grams. The mass range of the curcumin may be from about 10 milligrams to about 1500 milligrams.

The at least one anti-hyperandrogenism ingredient may include monacolin K (red yeast). The amount may include the monacolin K in a mass range from about 0.5 gram to about 4 grams. The mass range of monacolin K may be from about 1 gram to 3 about grams. The supplement may include CoQ10. The CoQ10 may be included at a mass range from about 0.5 milligram to about 4 milligrams.

The at least one anti-hyperandrogenism ingredient may include a bio-assimilable form of zinc ($Zn^{2+}$). The amount may include the zinc ($Zn^{2+}$) in a mass range from about 10 milligrams to about 50 milligrams. The mass range of the zinc ($Zn^{2+}$) may be from about 20 milligrams to about 30 milligrams. The zinc ($Zn^{2+}$) may be included in the form of zinc citrate.

The at least one anti-hyperandrogenism ingredient may include a bio-assimilable form of magnesium ($Mg^{2+}$). The amount may include the magnesium ($Mg^{2+}$) in a mass range from about 100 milligrams to about 500 milligrams. The mass range of the ($Mg^{2+}$) may be from about 200 milligrams to about 300 milligrams. The magnesium ($Mg^{2+}$) may be included in the form of magnesium citrate.

The at least one anti-hyperandrogenism ingredient may include a bio-assimilable form of chromium ($Cr^{3+}$). The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The at least one anti-hyperandrogenism ingredient may include inositol. The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The supplement may also include at least one other insulin-sensitivity modulating ingredient.

The composition combinations and mass ranges may constitute a dietary supplement for alleviation of symptoms of PCOS, with the supplement including a therapeutically effective amount of a combination of curcumin and inositol. The amount may include a daily dosage amount.

The curcumin may include curcuminoids in turmeric root extract. The amount may include the curcumin in a mass range from about 5 milligrams to about 2 grams. The mass range of the curcumin may be from about 10 milligrams to about 1500 milligrams.

The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The supplement may also include at least one other insulin-sensitivity modulating ingredient. The supplement may also include at least one other anti-hyperandrogenism ingredient.

The supplement may include OTC commercially available Provation Life® Inositol Plus, providing a flavored powder containing insulin-sensitivity modulating ingredients and anti-hyperandrogenism ingredients. Those ingredients may include, in amounts and proportions in the ranges described above: inositol, berberine, chromium, potassium, folate, red yeast, cinnamon, turmeric, coQ10, magnesium, zinc.

Methods

Methods for treating PCOS may include use of any of the composition combinations in any of the mass ranges. Several such methods are now presented.

The composition combinations and mass ranges may be utilized in a method for treatment of PCOS by oral administration of a therapeutically effective amount of a combination of curcumin and at least one other insulin-sensitivity modulating ingredient.

The curcumin may include curcuminoids in turmeric root extract. The amount may include the curcumin in a mass range from about 5 milligrams to about 2 grams. The mass range of the curcumin may be from about 10 milligrams to about 1500 milligrams.

The method's at least one other insulin-sensitivity modulating ingredient may be selected from a group consisting of inositol, cinnamon, chromium and berberine.

The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The cinnamon may include Ceylon cinnamon powder. The amount may include the cinnamon in a mass range from about 250 milligrams to about 1000 milligrams. The mass range of the cinnamon may be from about 400 milligrams to about 600 milligrams.

The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The berberine may include extract of *Berberis aristata* bark. The amount may include the berberine in a mass range from about 5 milligrams to about 2000 milligrams. The mass range of the berberine may be from about 7.5 milligrams to about 1500 milligrams.

The composition combinations and mass ranges may be utilized in a method for treatment of PCOS by oral administration of a therapeutically effective amount of a combination of curcumin and at least one anti-hyperandrogenism ingredient.

The curcumin may include curcuminoids in turmeric root extract. The amount may include the curcumin in a mass range from about 5 milligrams to about 2 grams. The mass range of the curcumin may be from about 10 milligrams to about 1500 milligrams.

The method's at least one anti-hyperandrogenism ingredient may be selected from a group consisting of inositol, chromium, zinc, magnesium and monacolin K (red yeast).

The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The amount may include the zinc ($Zn^{2+}$) in a mass range from about 10 milligrams to about 50 milligrams. The mass range of the zinc ($Zn^{2+}$) may be from about 20 milligrams to about 30 milligrams. The zinc ($Zn^{2+}$) may be included in the form of zinc citrate.

The amount may include the magnesium ($Mg^{2+}$) in a mass range from about 100 milligrams to about 500 milligrams. The mass range of the ($Mg^{2+}$) may be from about 200 milligrams to about 300 milligrams. The magnesium ($Mg^{2+}$) may be included in the form of magnesium citrate.

The amount may include the monacolin K in a mass range from about 0.5 gram to about 4 grams. The mass range of monacolin K may be from about 1 gram to 3 about grams. The method may include the administration of CoQ10. The CoQ10 may be included at a mass range from about 0.5 milligram to about 4 milligrams.

The composition combinations and mass ranges may be utilized in a method for treatment of PCOS by oral administration of a therapeutically effective amount of a combination of monacolin K (red yeast) and at least one other anti-hyperandrogenism ingredient.

The amount may include the monacolin K in a mass range from about 0.5 gram to about 4 grams. The mass range of monacolin K may be from about 1 gram to 3 about grams. The method may include the administration of CoQ10. The CoQ10 may be included at a mass range from about 0.5 milligram to about 4 milligrams.

The method's at least one other anti-hyperandrogenism ingredient may be selected from a group consisting of inositol, chromium, zinc and magnesium.

The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The amount may include the zinc ($Zn^{2+}$) in a mass range from about 10 milligrams to about 50 milligrams. The mass range of the zinc ($Zn^{2+}$) may be from about 20 milligrams to about 30 milligrams. The zinc ($Zn^{2+}$) may be included in the form of zinc citrate.

The amount may include the magnesium ($Mg^{2+}$) in a mass range from about 100 milligrams to about 500 milligrams. The mass range of the ($Mg^{2+}$) may be from about 200 milligrams to about 300 milligrams. The magnesium ($Mg^{2+}$) may be included in the form of magnesium citrate.

The composition combinations and mass ranges may be utilized in a method for treatment of PCOS by oral administration of a therapeutically effective amount of a combination of monacolin K (red yeast) and at least one insulin-sensitivity modulating ingredient.

The amount may include the monacolin K in a mass range from about 0.5 gram to about 4 grams. The mass range of monacolin K may be from about 1 gram to 3 about grams. The method may include the administration of CoQ10. The CoQ10 may be included at a mass range from about 0.5 milligram to about 4 milligrams.

The method's at least one insulin-sensitivity modulating ingredient may be selected from a group consisting of inositol, cinnamon, chromium and berberine.

The inositol may include myo-inositol. The inositol may include the mixture of myo-inositol and D-chiro-inositol. The amount may include the inositol in a mass range from about 0.5 gram to about 4 grams. The mass range of the inositol may be from about 0.75 grams to about 2 grams.

The cinnamon may include Ceylon cinnamon powder. The amount may include the cinnamon in a mass range from about 250 milligrams to about 1000 milligrams. The mass range of the cinnamon may be from about 400 milligrams to about 600 milligrams.

The amount may include the chromium ($Cr^{3+}$) in a mass range from about 200 micrograms to about 1000 micrograms. The mass range of the ($Cr^{3+}$) may be from about 300 micrograms to about 800 micrograms. The chromium ($Cr^{3+}$) may be included in the form of chromium picolinate.

The berberine may include extract of *Berberis aristata* bark. The amount may include the berberine in a mass range from about 5 milligrams to about 2000 milligrams. The mass range of the berberine may be from about 7.5 milligrams to about 1500 milligrams.

The methods may include oral administration of the OTC commercially available Provation Life® Inositol Plus powder, typically mixed into beverage or food, with a typical recommended daily intake of 5¼ grams of the homogeneously dry-mixed powder.

CASE STUDIES

Patient A, a 22 year old female, had been unsuccessful conceiving over 12 months. She has been married for two years and was on birth control pills prior to attempting to conceive. Once she stopped her pills, her menstrual cycles became erratic, inconsistent and, at times, absent. From a detailed history, laboratory work-ups and examination, it was clear that she met diagnostic criteria for PCOS. (According to the Rotterdam criteria, a clinical diagnosis of PCOS requires that a patient present with two of the following symptoms: Oligo-ovulation or anovulation; hyperandrogenism; clinical signs (such as hirsutism) or biological markers (such as a raised free-androgen index or free testosterone).

Patient A was started on the nutraceutical combination supplements and was encouraged to remain compliant. Within six weeks, she regained her menstrual cyclicity, indicating she was ovulating. Ovulation was confirmed by laboratory analysis and, twelve weeks later, patient A successfully conceived, after over 12 months of infertility, with no exogenous hormone treatment.

Patient B, a 26 year old female, with menarche at age 12, had been having regular periods then for two-three years, after which she began to experience irregular menstrual flow. By age 21, her menstrual cycles ceased almost entirely. Since then, she has had very infrequent cycles, one to two per year. She suffered from acne and irregular hair growth (on face and chest). Her laboratory work-ups and examinations indicated that she fit the diagnostic criteria for PCOS.

Patient B was started on the nutraceutical combination supplements and, within two months, she regained her menstrual cyclicity and also lost 5 kilograms of body mass. While her acne improved relatively quickly, her hair growth took an additional three months to show signs of improvement. She noted later, in retrospect, that when she was compliant with the supplement regimen, her cycle was regular; and that when she was not compliant, she did not get her period.

Patient C, a 29 year old female, had experienced irregular menses for 10 years but had not pursued medical examination/intervention during that time to address the issue. In her history, she also reported excess hair growth in unwanted areas and that she had performed cosmetic depilatory procedures in response. She was married for two years and had not conceived in the 24 months prior to presenting seeking help conceiving. Laboratory work-ups confirmed a diagnosis of PCOS.

Patient C was started on the nutraceutical combination supplements. Additionally she was referred to an infertility specialist secondary to patient intent and desire to conceive quickly. During the timespan of the infertility work-up, prior to receiving any interventional hormonal therapies, she conceived with only the nutraceutical combination supplements as an aid.

Medical research has been conducted on application of the compositions and methods disclosed herein for dietary alleviation of PCOS, using the OTC commercially available Provation Life® Inositol Plus product at its recommended daily dosage of about 5.25 grams. In the multiple case studies presented, baseline levels of at least three pertinent hormones—lutenizing hormone (LH), follicle-stimulating hormone (FSH) and luteal-phase progesterone—were assayed upon patient intake and then after several months of treatment by oral administration of the product. (The assay levels for the three hormones are given herein in milli-International Units per milliliter serum.) The time interval between intake and follow-up assays ranged from two to six months.

Intake baseline levels were consistent with the anovulatory symptomology for which the patients were seeking treatment, with luteal-phase progesterone below 3.0 in all cases. In seven studies for which multi-month follow-up assay levels were available as of this writing, the average intake baseline luteal-phase progesterone was about 1.3, while the average post-treatment follow-up value was about 11.8, with ovulation achieved in six of the seven cases, and pregnancy in two of those six. The single case in which anovulatory symptomology was not reversed presented a lower luteal-phase progesterone level after multi-month product use than at intake. That case may serve as a reminder that the full range of underlying causes of PCOS may include those not targeted by the compositions and methods given herein.

For the seven case studies, the intake and follow-up hormone levels (presented below in order of increasing intake baseline luteal-phase progesterone level, and noting the number of months (mo.) of treatment between intake and follow-up), with luteal-phase progesterone levels given as A; LH levels, as B; and FSH levels, as C. Also noted are results as of the follow-up, including a rough measure of shift of patient's LH/FSH ratio of greater than 1 that is typical of PCOS to a healthier ratio of less than 1.

| Case I | | | |
|---|---|---|---|
| Case I | Intake | 3 mo. | Results |
| A | 0.13 | 25 | Ovulatory |
| B | 6.2 | 0.66 | LH/FSH |
| C | 3.78 | 2.33 | corrected |

Case II

| Case II | Intake | 2 mo. | Results |
|---|---|---|---|
| A | 0.50 | 3.3 | Ovulatory |
| B | 5.5 | 2.4 | LH/FSH |
| C | 2.4 | 6.5 | corrected |

Case III

| Case III | Intake | 4 mo. | Results |
|---|---|---|---|
| A | 0.62 | 3.2 | Ovulatory |
| B | 6.4 | 4.2 | LH/FSH |
| C | 4.4 | 5.5 | improved |

Case IV

| Case IV | Intake | 2 mo. | Results |
|---|---|---|---|
| A | 1.2 | 6.0 | Ovulatory |
| B | 5.40 | 3.58 | LH/FSH |
| C | 3.30 | 2.74 | improved |

Case V

| Case V | Intake | 6 mo. | Results |
|---|---|---|---|
| A | 2.0 | 36.3 | Pregnant |
| B | 86.1 | 3.49 | LH/FSH |
| C | 10.0 | 8.86 | corrected |

Case VI

| Case VI | Intake | 2 mo. | Results |
|---|---|---|---|
| A | 2.2 | 7.8 | Pregnant |
| B | 4.2 | 2.88 | LH/FSH |
| C | 2.20 | 2.36 | improved |

Case VII

| Case VII | Intake | 2 mo. | Results |
|---|---|---|---|
| A | 2.7 | 0.84 | anovulatory |
| B | 22.3 | 5.1 | LH/FSH |
| C | 9.94 | 5.81 | improved |

All references cited in the present application are incorporated in their entirety herein by reference to the extent not inconsistent herewith.

Thus, compositions and methods for nutraceutical compositions and methods for dietary alleviation of polycystic ovary syndrome have been provided. Persons skilled in the art will appreciate that the present invention can be practiced by other than the described embodiments, which are presented for purposes of illustration rather than of limitation. The present invention is limited only by the claims that follow.

What is claimed is:

1. A dietary supplement for alleviation of symptoms of Polycystic Ovary Syndrome, the dietary supplement comprising a therapeutically effective amount of a combination of:
  a daily dosage amount of red yeast powder, which comprises monacolin K as an anti-hyperandrogenism ingredient, said monacolin K being in the form of a powder derived from white rice grown with red yeast, said daily dosage amount of the red yeast powder which comprises monacolin K having a mass of about 1 gram;
  turmeric root, which comprises curcumin as an insulin-sensitivity modulating ingredient, said turmeric root which comprises curcumin having a daily dosage amount having a mass of about 10 milligrams;
  at least one other insulin-sensitivity modulating ingredient, said at least one other insulin-sensitivity modulating ingredient including:
    ceylon cinnamon powder in a daily dosage amount having a mass of about 500 milligrams; and
    berberine in a daily dosage amount having a mass of about 10 milligrams;
  other anti-hyperandrogenism ingredients include:
    magnesium citrate in a daily dosage amount having a mass of magnesium of about 255 milligrams; and
    zinc citrate in a daily dosage amount having a mass of zinc of about 25 micrograms;
  dual-acting insulin-sensitivity modulating ingredient and anti-hyperandrogenism ingredient include:
    inositol in a daily dosage amount having a mass of about 1 gram; and
    chromium picolinate in a daily dosage amount having a mass of chromium of about 500 micrograms; and
  additional ingredients include:
    potassium in a daily dosage amount having a mass of about 20 milligrams;
    folate in a daily dosage amount having a mass of about 680 micrograms dietary folate equivalents; and
    coenzyme Q10 in a daily dosage amount having a mass of about 1 milligram;
  wherein:
    when a person who has symptoms of Polycystic Ovary Syndrome and who has a luteinizing hormone (LH) to follicle-stimulating hormone (FSH) ratio of greater than 1.0 takes a daily dose of the dietary supplement for 2 months or more, their LH to FSH ratio becomes less than 1.0.

* * * * *